United States Patent [19]
Ristol Debart

[11] Patent Number: 5,932,468
[45] Date of Patent: Aug. 3, 1999

[54] METHOD OF INACTIVATING VIRUSES IN PROTEINS

[75] Inventor: Pere Ristol Debart, Sabadell, Spain

[73] Assignee: Grupo Grifols, S.A., Barcelona, Spain

[21] Appl. No.: 08/742,502

[22] Filed: Nov. 1, 1996

[30] Foreign Application Priority Data

Nov. 3, 1995 [ES] Spain ..................................... 9502143

[51] Int. Cl.$^6$ ............... C12N 7/06; C12N 7/00; C12N 7/04; C12N 7/02
[52] U.S. Cl. ................. 435/238; 435/235.1; 435/236; 435/239
[58] Field of Search ................................. 435/236, 238, 435/239, 235.1

[56] References Cited

U.S. PATENT DOCUMENTS

| | | | |
|---|---|---|---|
| 3,941,696 | 3/1976 | Melnick et al. | 210/62 |
| 4,055,655 | 10/1977 | Maurer et al. | 424/294 |
| 4,721,777 | 1/1988 | Uemura et al. | 530/389 |
| 5,094,850 | 3/1992 | Mayr et al. | 424/89 |

FOREIGN PATENT DOCUMENTS

| | | |
|---|---|---|
| 0177836 | 9/1985 | European Pat. Off. . |
| A-0312839 | 4/1989 | European Pat. Off. . |
| A-0343275 | 11/1989 | European Pat. Off. . |
| 53-142593 | 12/1978 | Japan . |
| 62-283933 | 5/1986 | Japan . |
| A-9403590 | 2/1994 | WIPO . |
| 9422305 | 10/1994 | WIPO . |

OTHER PUBLICATIONS

Barrowcliffe, "Virological Safety Aspects of Plasma Derivatives," In: Dev. Biol. Stand., Brown F. ed., Basel, Karger, vol. 81, p. 125–135, 1993.

Voet & Voet "Three–Dimensional Structures of Proteins", In: Biochemistry, John Wiley & Sons, New York, 1990, pp. 144–192.

Suomela, Hannu, "Inactivation of Viruses in Blood and Plasma Products," Transfusion Medicine Reviews, vol. VII, No. 1 (Jan. 1993), pp. 42–57.

Roberts, P., "Virus Safety of Plasma Products," Reviews in Medical Virology, vol 6 (1996), pp. 25–38.

Grun, Janet B., White, Elizabeth M. and Sito, Alexander F., Viral Removal Inactivation by Purification of Biopharmeceuticals, BioPharm, vol. 5, No. 9 (Nov./Dec. 1992), pp. 22–30.

Cambridge Healthtech Institute, "Blood Safety & Screening" (Third Annual), (Apr. 14–16, 1997).

*Primary Examiner*—Donna C. Wortman
*Assistant Examiner*—Jay Williams
*Attorney, Agent, or Firm*—Darby & Darby

[57] ABSTRACT

An efficient industrial method, by incubation at extreme (alkaline) pH in a stabilized medium, of inactivating viruses in general (with or without a lipid envelope) in media containing proteins for therapeutic use, without denaturing or significant loss of biological activity.

27 Claims, No Drawings

METHOD OF INACTIVATING VIRUSES IN PROTEINS

DESCRIPTION

Therapeutic use of human plasma derivatives is never free from the risk of transmission of viruses, even after introduction of methods of selecting the plasma used as the starting material. In many cases, the presence of viral contamination is determined indirectly via serological markers (alanine aminotransferase) and via the presence of specific antibodies (human immunodeficiency virus: HIV types 1 and 2; hepatitis C virus: HCV). Consequently an incubation period is required before detectable quantities of the said indirect indicators appear. Abundant proliferation of the virus occurs during this post-infective period (the window period). Depending on the type of virus, this viraemia phase may last up to 3–6 months after the infection.

Thanks to the sensibility of existing methods of analysis, contaminated units can be detected in the first weeks after the infection (hepatitis B virus surface antigen: HBsAg), or a few weeks (2 or 3) or months (1 or 2) for HIV and HCV.

Human plasma blood derivatives are prepared from a very large number of plasma donations, usually far above 1000 individual units, so that there is a high statistical probability that a unit with a high charge of virus (and an analytically negative charge of antibodies) will be included during the "window period" and will contaminate the entire initial pool of plasma (see Alegre Amor, A.: La transmisión de enfermedades virales por productos sanguíneos. Congreso Hematología de Granada, Nov. 1994: 175–178).

Direct determination of the viral genome by the method of amplification and detection of the specific DNA, e.g. the polymerase chain reaction (PCR) is at present applied to the completed final product or in the initial pool of the starting plasma, so that a high minimum level of contamination is required in order to be detected.

Consequently a negative PCR value cannot be interpreted as total absence of viruses, in the same way as a positive value does not necessarily indicate viral infectiousness.

Consequently there are still good reasons for specific steps for inactivation or attenuation of viruses during the processes for production and purification of blood derivatives.

Up to recently there have been extensive publications concerning the transmission of infectious agents via blood derivatives, and research continues to concentrate on monitoring of methods of production in order to check that the plasma products are free from viruses.

Since absolute freedom from viruses is not attainable (owing to the possibility of unknown viruses) and in view of possible errors or departures from good production standards (GPS) in the preparation of blood derivatives, the present trend, particularly in the specific step of inactivation of viruses or as a result of cross-contamination, is to include a double specific inactivation step in the production processes, thus enormously reducing the risk of transmission of viruses (EEC Guide (CPMP): III/8115/89).

Likewise, current recommendations by health authorities regarding freedom from viruses are aimed at including a second inactivation step in general for every kind of virus, whether with or without an external lipid envelope.

With regard to the known viruses transmitted in plasma, those at present recognised as the most dangerous are the human immunodeficiency and the hepatitis viruses (particularly B and C), which can be inactivated by known methods.

Donations may also be contaminated by herpes virus (HSV and HHV) or cytomegalovirus (CMV), Epstein-Barr (EBV) or human immunoleucopathy virus (HTLV-I/II), although the likelihood of these passing into the plasma is remote in view of the strong attachment to cells (leucocytes) which are previously separated.

Other viruses such as hepatitis A and human parvovirus (PVH B19) may be present in the plasma, mainly the last-mentioned substance, since the incidence in the donor population is relatively high. The two last-mentioned viruses are those transmitted by plasma which offer most resistance to inactivation by physical and chemical agents, although they can be considered less dangerous than the others, always provided the infection occurs in healthy patients. Human parvovirus is potentially dangerous in immunodepressed individuals or during treatment of pregnant women (danger to the foetus) (see Mosquet, N. et al.: Atteinte hématologique sévere lors d'une infection à parvovirus B19: Des injections d'antithrombine III sont-elles à origine de la contamination? Therapie 1994; 49: 459–76).

In any case, a second inactivation step should be supplemented by other known methods of inactivation capable of killing the most resistant viruses not provided with a lipid envelope. The methods need to be monitored with regard to some of these viruses or models thereof.

To date, the methods of elimination of viruses described in the art are based on physical and chemical mechanisms which reduce contamination by inactivation and/or fractionation. The most well-established present-day methods can be classified in the following order:

Chemical treatment with solvent (tri-n-butyl phosphate and alkyl phosphate derivatives or TNBP) and detergent (Tween-80 or polysorbate, triton X-100 or nonionic surface-active derivatives), symbol S/D (see Horowitz, B. et al.: Inactivation of viruses in labile blood derivatives: I. Disruption of lipid-enveloped viruses by Tri-(n-butyl)phosphate detergent combinations. Transfusion 1985; 25: 516–522).

Pasteurisation in liquid at 60° C. for 10 hours in the intermediate or final step, in the presence of stabilisers (see Uemura, Y. et al.: Inactivation and elimination of viruses during the fractionation of an intravenous immunoglobulin preparation. Vox. Sang. 1989; 56: 155–61).

Dry heat treatment (dry HT) in the intermediate step or in the completed final phial (usually) at temperatures $\geq 80°$ C., with prolonged exposure (see Knevelman, A. et al.: Effect of Monosaccharides during Severe Dry Heat Treatment of Coagulation Factor VIII Concentrates. Vox. Sang. 1994; 66: 96–103).

Nanofiltration or filtration of viruses through membranes having uniform pores smaller in size than the virus (see Burnouf-Radosevich, M. et al., Nanofiltration, a New Specific Virus Elimination Method Applied to High-Purity Factor IX and Factor XI Concentrates. Vox. Sang. 1994; 67: 132–138).

The following other methods are less used or have fallen into disuse: dry heat-treatment with organic solvents, inactivation with β-propiolactone-UV (BPL-UV), methylene-UV blue (see Wagner, S. J. et al.: Mammalian genotoxicity assessment of methylene blue in plasma: implications for virus inactivation. Transfusion 1995; 35 (5): 407–413), treatment at moderately acid pH (applicable only to gammaglobulin) (see Kempf C. et al.: Virus inactivation during production of intravenous immunoglobulin. Transfusion 1991; 31 (5): 423–27).

In general, these methods are efficient at attenuating or separating viruses though not all eliminate the virus efficiently and none of them can ensure total absence or significant attenuation of all types of viruses. Consequently each method has advantages and disadvantages.

A viral elimination step should ideally meet various requirements, some of which are not covered by the most widely-used methods of inactivation at present. These requirements are as follows:

1. When a number of methods of inactivation are applied to the same purification process, they should act via different mechanisms. For example, physical methods (inactivation or fractionation) form good combinations with chemical methods (inactivation).

2. The methods should be active against any type of virus. Methods of inactivation have limited or no effect on viruses having higher physical and chemical resistance such as the viruses without a lipid envelope (treatment with S/D is ineffective against these viruses, or of reduced effect with BPL-UV or methylene-UV blue and dry heat treatment at temperatures below 80° C.). Pasteurisation in principle is an effective method of inactivating any type of virus, but its effect is compromised when the concentration of stabilisers or protein is very high, owing to a mechanism of protection of viruses, so that the reduction is insignificant in the case of the most heat-resistant viruses in media containing high concentrations of stabilisers and/or proteins.

Filtration of viruses through a membrane reduces any kind of virus irrespective of its physical and chemical resistance, but depends on the size of the viruses relative to the pores of the membrane. Consequently the smallest viruses cannot be totally eliminated, and unfortunately most of these are without a lipid envelope (human parvovirus, hepatitis A and polio virus).

3. The method must not induce biological inactivation or denaturation of proteins, or the effect must be very small and in no case must result in materials with an antigen response. Some methods of chemical inactivation result in a chemical alteration in the proteins (BPL-UV) and similarly heat treatment, dry or liquid (pasteurisation) almost inevitably results to some extent in denaturation of proteins, either of the molecule in question or of accompanying contaminating proteins.

4. Possibility of inclusion in the final step. Chemical inactivation is difficult in the final step owing to the need to separate the chemical reagents used (S/D, BPL, thiocyanate), except for the method of inactivation by methylene blue (even so, it should be remembered that the by-products of this reaction are not completely innocuous). Also, some pasteurisation processes are performed in an intermediate step owing to the need for subsequent elimination of denatured material and/or of the stabilisers used. Dry heat treatment is frequently applied in the final phase or in the finished phial.

Nanofiltration in general is included in the final finished bulk solution, in such a way that subsequent manipulation is not required in certain applications.

5. There must not be any toxic residues due to the inactivation step (chemical reagents). Most chemical treatments require subsequent steps for efficient elimination of the reagents. The maximum permissible limits should be established in dependence on the toxicity of the chemical contaminant and the frequency of administration of the preparation (as in the previously-mentioned cases of S/D. BPL and thiocyanate). Methods of inactivation (by heating) or fractionation (nanofiltration) are of course free from these disadvantages.

6. operation should be possible on an industrial scale and the processes should be completely reproducible and should be subject to monitoring of known parameters which are easy to adjust. Chemical inactivation is affected by the concentration of the products (proteins, salts, stabilisers and chemical reagents) in addition to the temperature and length of exposure. Occasionally, however, some uncontrolled parameters may facilitate consumption of the said inactivating agents (when a chemical reaction occurs) or the starting solution for inactivation may be under non-reproducible conditions (presence of particles and sediments, etc). Inactivation by dry heat treatment (finished phial) depends on the residual moisture content of the phials, which may easily vary from batch to batch, so that this parameter cannot be properly monitored.

7. Preference is given to simple methods which do not require complementary purification steps. As already mentioned in Item 5 hereinbefore, chemical inactivation requires subsequent steps for elimination of toxic reagents. In addition, it will affect those methods of pasteurisation which require high stabilisation for protection of the protein (pasteurisation of FIX, FVIII, ATIII, $\alpha$1-PI, IM or IV gammaglobulins, etc).

8. The methods of inactivation must be of use on an industrial scale and at acceptable cost, with regard to materials and the reagents used. Nanofiltration is one case where the equipment is scrapped after being used once, and the productivity in grams of protein per hour and per unit surface is small and consequently industrial application is limited to low production rates of proteins.

Finally, inactivation of viruses without a lipid envelope continues to be the subject of numerous studies with the aim of showing the virucidal efficacy of new methods and the safety of inactivation as regards possible alteration of the treated protein (see Highsmith, F. A. et al.: Inactivation of lipid-enveloped model viruses in normal human plasma by crosslinked starch-iodine. Transfusion 1994; 34: 322–327).

As stated previously, human parvovirus (PVH B19) and hepatitis A virus are the main viruses without a lipid envelope which are transmitted in human plasma or blood derivatives. Consequently, development of a second inactivation step should be directed mainly to reduction of these viruses.

Transmission of human parvovirus and hepatitis A has been detected in haemophiliac patients via administration of AHF inactivated exclusively with S/D. There are also descriptions of infection with human parvovirus by infusion of AHF inactivated by pasteurisation. It has also been shown that pasteurisation of proteins in stabilised media at high concentrations also protect the viruses, and the reduction in infectiousness is insignificant as regards the viruses PVH B19 and HAV.

There are recently-published descriptions of some cases of complications in the fetus after administration of anti-thrombin III preparations to pregnant mothers (see Mosquet, N. et al.: Atteinte hématologique sévere lors d'une infection à parvovirus B19: Des injections d'antithrombine III sont-elles à origine de la contamination? Therapie 1994; 49: 459–76). These cases are due to contamination with human parvovirus, which is itself a reason for contra-indication treatment, in view of the risk-benefit ratio and the possibility of alternative treatment.

The main object of the invention is efficient inactivation of viruses with or without a lipid envelope in a medium containing proteins from biological fluids, by virucidal treatment at extreme alkaline pH, under conditions where the proteins are not denatured by the protection provided by the stabilising agent.

The present introduction on the one hand substantiates the use of specific methods of inactivation such as the double inactivation step for reducing the risk of viral transmission. This introduction also shows the requirements on an ideal method of inactivation, showing that this continues to be an object of the art and a subject of investigation. This introduction also describes a case of specific contra-indication regarding administration of blood derivatives (antithrombin III) if steps for reduction of viruses without a lipid envelope are not included.

The present state of the art does not achieve the basic objectives of the invention with regard to effective low-cost elimination of viruses without a lipid envelope, mainly in the case of products contra-indicated for therapeutic use owing to suspected presence of resistant viruses (human parvovirus) in the end-product (antithrombin III) (see Mosquet, N. et al.: Atteinte hématologique sévere lors d'une infection à parvovirus B19: Des injections d'antithrombine III sont-elles à origine de la contamination? Therapie 1994; 49: 459–76).

Likewise there is no previous description or documentation of a method of inactivation at extreme (alkaline) pH directly intended for proteins for therapeutic use. The only thing known is the potential ability of alkalis to kill some viruses, so that this method has been used as a method of disinfection in chromatographic columns, ultrafilters and other re-usable equipment in order to avoid cross-contamination between batches, but the method has never been used for viral inactivation of plasma proteins used intravenously in therapy.

The possibility of inactivation at extreme alkaline pH is based on the stability of the protein and the protective effect obtained by the method described in the invention. This method, based on a mechanism of action on proteins in general, is completely novel and, as already explained, has indications which are not at present covered by any of the techniques described.

The only prior publications relate to applications of viral inactivation of gammaglobulin at moderately acid pH (pH 4) and therefore different from the invention, with incubation at a temperature of 37° C. and the synergic effect of proteolytic enzymes (pepsin), resulting in effective reduction of some viruses (see Kempf C. et al.: Virus inactivation during production of intravenous immunoglobulin. Transfusion 1991; 31 (5): 423–27).

The infectiousness of unstable viruses is effectively reduced under other conditions, at moderately acid pH (pH 4.25) and in the end-product (gammaglobulin and maltose) at 21° C. during 20 days of incubation, but there is no significant reduction of viruses without a lipid envelope.

However, the main objective of the invention (inactivation of viruses without a lipid envelope) has not been satisfactorily achieved to date, and the method used to achieve this objective (inactivation at extreme alkaline pH in the presence of a stabiliser), which has not been introduced for this purpose until now, also gives absolute novelty to the invention as a whole.

The invention is based on the capacity to inactivate viruses (with or without a lipid envelope) at extreme pH conditions of the medium.

Results have already been published on viral inactivation in a moderately acid medium and in the presence of stable acid proteins (gammaglobulin) by addition of mineral (hydrochloric) acid or weak acids (citric, acetic, etc). As described, significant inactivation is obtained in the case of more sensitive viruses, mainly those with a lipid envelope (the human herpes virus and the murine leukaemia virus X-I). However, in order to obtain significant reduction of viruses at pH 4, it is necessary to incubate the protein solution at an above-ambient temperature (37° C.), thus totally inactivating the model viruses with a lipid envelope, except for the vesicular stomatitis virus (VSV), which continues to be infectious.

Inactivation in the cold (4° C.) is ineffective for most viruses, so that incubation at 37° C. acts synergetically with the acid pH (see Kempf C. et al.: Virus inactivation during production of intravenous immunoglobulin. Transfusion 1991; 31 (5): 423–27).

There have also been previous descriptions of inactivation of viruses in the final phial of gammaglobulin at pH 4.25 (with its maltose excipient) at 21° C. for 20 days, which shows that viruses with less physical and chemical resistance are totally inactivated, but not the more resistant viruses without a lipid envelope (simian virus-40; Reovirus-3).

Also, the resistance of certain viruses to acid media such as polio virus or hepatitis A is known and has been described (see Roberts, Peter L. et al.: Removal and Inactivation of Enveloped and Non-enveloped Viruses during the Purification of a High-Purity FIX by Metal Chelate Affinity Chromatography. Vox. Sang. 1994; 67 (1): 69–71). In these cases the reduction of infectiousness is practically zero.

With regard to inactivation in a basic medium, there is a description in the prior art of the virucidal efficacy of disinfection of equipment (columns, ultrafilters, etc) with alkaline solutions, thus avoiding cross-contamination between processed batches (see Grun, Janet B. et al.: Viral Removal/Inactivation by Purification of Biopharmaceuticals. BioPharm 1992; 5 (9): 22–30), although the method has never been applied to specific viral inactivation for proteins for therapeutic use, under extreme pH conditions.

Research by the inventors has shown the virucidal effect of alkaline hydroxides at extreme pH in the absence of proteins or other stabilisers or excipients. The results obtained with regard to viruses with or without a lipid envelope show high virucidal efficiency against both types of virus. Accordingly, the polio A virus (a model for hepatitis A) and canine parvovirus (a model for its human homologue) can both be inactivated.

Also the method according to the invention at extreme alkaline pH is based on a different mechanism of action from inactivation by pasteurisation, so that the methods can presumably be added and complement one another.

The possibility of inactivating viruses in the presence of proteins at extreme pH will to a great extent depend on the stability of the proteins in the medium. Some proteins have greater structural stability in the basic pH zone, so that the method according to the invention is mainly directed towards this type of moderately stable proteins, such as inhibitors of serine-protease and related enzymes, from which we pick out antithrombin (ATIII), α1 of protease inhibitor (α1-antitrypsin) and human albumin (which has a certain structural resemblance to the molecules of serine-protease inhibitors).

For the purpose of inactivation at extreme alkaline pH, the proteins have to be stabilised to avoid denaturing.

Various compounds for stabilising proteins in general have been described, the usual aim being to preserve the molecular integrity during the steps of inactivation by pasteurisation or during heat-treatment, and to maintain the biological activity in the final end-product, either in liquid or freeze-dried formulations. The large number of compounds used are in the following main groups:

sugars, alcohol-sugars and polyols (saccharose, maltose, mannitol, sorbitol, dextrins, polyethylene glycol, etc)
amino acids (lysine, glycine, histidine, arginine, etc)
proteins (albumin) and
organic acids or salts thereof (caprylate, citrate, EDTA, etc).

Inorganic salts have also been used as excipients at physiological concentrations, the only aim being to obtain adequate isotonicity and solubility (mainly in the case of freeze-dried), the main substances being sodium chloride, sodium phosphate, etc.

The specific case of stabilisation of proteins at extreme pH, for the purpose of viral inactivation, has not been touched on before the present invention. It would therefore be assumed that the general methods previously described are applicable.

However, these methods do not sufficiently protect the proteins to be inactivated.

As a result of the research by the inventors, it has been possible to stabilise proteins without introduction of external agents, which are potentially toxic or difficult to eliminate, the aim being to bring about inactivation at alkaline pH.

The theory of stabilisation of proteins by treatment at extreme pH is based on hypothetical hydrophobic interaction of the proteins and variation in the molecular size (folding) due to the reversible action of high concentrations of salts (such as sodium chloride) in the solution. This molecular contraction assists the preservation of the biologically active regions due to repulsion of charges (solvent) resulting from the greater exposure of the more water-repellent zones.

The stabilising agents can be any type of inorganic salts, especially poly-ionic, capable of providing the medium with a sufficient ionic charge (e.g. ammonium sulphate, sodium chloride, etc.).

On the other hand, the possibility of also stabilising the viruses when the ionic strength increases will be more remote, since the external envelope is formed by rigid protein or lipoprotein structures and therefore has little opportunity to protect itself by contraction and hydrophobicity.

The invention describes a method of inactivating viruses in general at extreme basic pH in protein solutions which are stable for subsequent therapeutic use and are of human or animal origin or obtained by the technology of recombinant DNA.

Generally the inactivation treatment is applied in a final phase of the production process, so as to avoid the possible risk of residual contamination of the previous steps. It is also preferable to use fractions with sufficient purity to avoid unnecessary precipitation or separation after the treatment.

The following non-limitative examples of application of the invention refer to proteins such as antithrombin (ATIII), α1 proteinase inhibitors (α1-PI) or sero-albumin.

The starting solubilised protein solution or fraction can be obtained from Cohn, Cohn-Oncley, Kistler-Nischmann fractionation with ethanol in the cold, or with polyethylene glycol, octanoic acid, ion-exchange or affinity chromatography, or any other method which yields sufficiently pure fractions for inactivation treatment at extreme alkaline pH.

The first step is to solubilise the protein and preferably reduce excipients and salts, if present in significant quantities. It is also necessary to eliminate or significantly reduce the possible presence of denaturing agents in the protein solution (e.g. ethanol). The method of doing this is by gel filtration by for molecular exclusion resins(commercial makes: Sephadex, Sepharose, Sephacryl, Ultragel, Sephacel, etc) or preferably the method of diafiltration against water through ultrafiltration membranes from 1 to 50 kD molecular pore size (Pellicon model, by Millipore) depending on the size of the protein. An alternative method is conventional dialysis with nitrocellulose, cellophane or cuprophane membranes (make: I DEL M-11) until the dialysed solution preferably has an osmolality value below 300 mOsm/kg, though this value is not limitative if the value of the ionic strength of the protein solution is subtracted from the required added quantity of stabiliser.

The solution is then suitably diluted with water for injection to between 25% and 0.001% of the protein concentration (depending on the solubility of the protein in question), preferably between 5% and 0.1%, depending on the protein to be inactivated.

The solution is adjusted at a temperature between 0 and 45° C., preferably between 2 and 4° C. depending on the protein.

An amount of a neutral or non-neutral ionic salt from 0.005 mols to saturation (a chloride or sulphate of alkali metals or the ammonium ion, or alkaline salts of carboxylic acids, etc) is added to the solution together with preferably 1 to 4 mols per kg of actual solution of sodium chloride, alone or mixed with other salts capable of providing sufficient ionic strength to the solution. The excipients or stabilisers forming part of the final composition of the product can be added simultaneously if necessary, together with other particular substances, always provided they are resistant to the extreme pH during processing.

When the protein solution has been stabilised, a solution of alkaline metal hydroxide (preferably from 0.001 M to saturation) is added with agitation, or any other alkaline solution which is compatible with the protein and the medium, provides a sufficient concentration of hydroxyl ions and can bring the solution to a pH between 10.0 and 14.0, preferably between pH 12 and 13. The temperature of the solution is kept between 0 and 45° C., preferably between 2 and 4° C.

The pH can be adjusted by any commercial pH-meter (made by Crison, Hanna), but a correct adjustment should be made previously with borate buffer at pH 10.00.

The exposure time during treatment is the minimum possible, less than or equal to 100 hours and greater than incubation for 1 second, preferably between 1 and 60 minutes, corresponding to treatment at extreme pH and short exposure.

After the exact incubation time, the solution is brought to pH <10 immediately, by addition preferably of hydrochloric acid, or by using another strong or weak mineral or organic acid, preferably, or by any other system capable of reducing the pH to a value near neutrality or the desired value.

The protein solution can then be dialysed and adjusted to the final formulation, preferably by use of sterilised throwaway dialysis cartridges (1 DEC M-11 or equivalent) or by using ultrafiltration membranes, preferably 1 to 50 kD (Pellicon model, by Millipore), using sufficient dialysis solution of suitable composition for the desired final formulation, in order appropriately to reduce the ionic strength of the solution.

The adjusted bulk solution can be sterilised by filtration with a 0.22 μm membrane and can subsequently be dispensed in phials for presentation in liquid form, or freeze-dried if appropriate.

EXAMPLES OF THE INVENTION

Example 1

The effectiveness of alkaline treatment for inactivation of viruses was tested by inoculating 1 ml of virus concentrate into 19 ml of 0.1 N sodium hydroxide solution at a temperature of 4° C., resulting in a pH between 12.5 and 13.

At the times specified in Table No. 1, samples were for cultivation of cells, after neutralisation with acid.

The assayed viruses were bovine herpes virus or BHV (virus with lipid envelope) and canine parvovirus or CPV and human polio virus type 2 (both viruses without a lipid envelope). The counts were made via the cytopathic effect in the cultivation cells ($TCID_{50}$).

The results are shown in Table 1.

TABLE 1

Inactivation of viruses (with or without lipid envelope) with sodium hydroxide
VIRUS COUNT (total units)

| Time (min) | CPV | BHV | POLIO |
|---|---|---|---|
| Inoculum | $2.0 \times 10^9$ | $6.9 \times 10^9$ | $7.1 \times 10^8$ |
| 0 | $1.9 \times 10^3$ | $1.2 \times 10^2$ | $3.5 \times 10^4$ |
| 10 | $2.4 \times 10^3$ | $1.2 \times 10^2$ | $2.7 \times 10^3$ |
| 20 | $9.6 \times 10^2$ | $4.5 \times 10^1$ | $2.0 \times 10^4$ |
| 60 | $5.0 \times 10^3$ | $4.5 \times 10^1$ | $2.1 \times 10^3$ |
| Inactivation: Reduction factor (log) | 5.6 | 8.2 | 5.5 |

Alkaline inactivation treatment results in significant reduction of viruses ($\geq 4$ log) with regard to the three viruses assayed, and can therefore be considered as a specific inactivation step.

Example 2

Viral monitoring of the inactivation step was carried out by the method according to the invention. This was done by assaying two different viruses, i.e. bovine herpes virus and canine parvovirus.

The protein to be inactivated was final purified antithrombin III (lot no. 5139) with specific activity above 7 IU/mg protein and a protein concentration of 0.8%. 45.1 g of antithrombin III solution was taken for each virus to be assayed, and 8.7 g of sodium chloride stabiliser, 0.81 g trisodium citrate dihydrate and 1.06 g mannitol were added respectively and in the stated order as excipients. After each addition, the combined product was solubilised. The solution was then cooled in a water/ice bath to 1.0±0.5° C., while continually adding 4.5 g of the inoculum of each virus, and taking a 10 g sample after mixing. 1.75 ml of 2N sodium hydroxide was added, so that the pH of the solution was 12.50±0.05. After treatment for 1 hour under these conditions, each assay was neutralised. This was done by introducing 1.55 ml of 2N hydrochloric acid and checking that the pH was between 6.7 and 6.9.

The final samples of each assay were cultivated in the corresponding growth cells in order to quantify the reduction in infectiousness obtained by the method. The count was made by assay of cytopathogenicity $TCID_{50}$.

The results are given in the following Table 2:

TABLE 2

Inactivation of viruses (with and without lipid envelope) in concentrated, purified antithrombin III
VIRUS COUNT (total units)

| Sample | BHV | CPV |
|---|---|---|
| Inoculum | $1.4 \times 10^9$ | $2.4 \times 10^7$ |
| Filler (starting material) | $2.2 \times 10^8$ | $4.2 \times 10^7$ |
| Time = 60 min | $<1.5 \times 10^3$ | $8.0 \times 10^2$ |
| Inactivation: Reduction factor (log) | $\geq 5.2$ | 4.7 |

The values obtained for reduction of viruses are significant ($\geq 4$ log) for the two viruses under study. In the specific case of canine parvovirus, the level of reduction is practically the same as in the absence of protein and stabilisers (Example 1), the residual infectiousness being below the limit of measurement ($8.0 \times 10^2$ units).

Example 3

For the purpose of characterising the inactivated product by treatment at extreme pH, the process according to the invention was carried out until the final freeze-dried product was obtained (antithrombin III).

A starting antithrombin III concentrate of 85.3 g purified by double affinity chromatography (lot 0.5/1) with optical density ($A_{280\ nm}$) of 4.20 and activity 43.1 IU/ml was stabilised with sodium chloride, adding 3 mols per liter of actual solution.

The solution was then adjusted with suitable excipients in the proportion of 20 g of trisodium citrate dihydrate and mannitol respectively per liter of initial solution. The solution was then cooled in a water/ice bath and kept at 3±1° C. during the entire process. 2N sodium hydroxide was then added until the pH was 12.50±0.02 (Crison pH-meter, calibrated with borate buffer at pH 10.00). Incubation for 1 hour was followed by neutralisation with 2N hydrochloric acid until the pH was near neutrality.

The inactivated solution of viruses was diafiltered to a constant volume in an aseptic ultrafiltration cartridge of 10 kD molecular section (model TFF PrepScale, 2.5 sq. ft. by Millipore), using a total of five volumes of dialysis buffer solution containing sodium chloride, sodium citrate and mannitol. The resulting solution was adjusted to the required power and sterile-filtered through a 0.22 μm membrane and dispensed in phials which were then freeze-dried.

The final finished product was characterised in order to show any possible molecular alterations.

The protection provided by the stabiliser (sodium chloride) during alkaline treatment was shown by determining the recovery of activity and the specific activity during the inactivation step. The values obtained are shown in the following Table 3.

TABLE 3

Recovery of activity and specific activity of ATIII during the inactivation step at extreme pH (12.5)

| Sample | ATIII activity (IU/ml) | Optical density (A 280 nm) | Units ATIII (IU) | % recovery of activity | Specific activity (IU/mg) |
|---|---|---|---|---|---|
| Stabilized ATIII solution | 43.1 | 4.20 | 3332 | 100 | 8.1 |
| ATIII solution after inactivation (1 hour at 3 ± 1° C.) | 39.3 | 3.95 | 3143 | 97.0 | 7.9 |

The finished product was characterised on the basis of tests confirming its functionality:

Heparin affinity: excluded (no affinity)=3%
(Heparin resin eluted=90% Sepharose 6FF)
Immunoelectrophoresis
crossed with heparin: slow forms (low affinity)=4.2%
Molecular distribution: aggregation (polymers)=3.6% (HPLC)
Electrophoresis
(cellulose acetate/amide black): band $\alpha_2$=99.6%
Specific activity: IU/mg total protein=7.9
(*) Molecular weights: SDS-PAGE=58,500 (single band)
  Reducing conditions=68,500 (single band) (2-ME)
(*) Isoelectro focus (isoelectric point)=4.98 principal band 4.90 secondary band
(*) The results were the same for ATIII purified in the finished phial, with or without the inactivation treatment according to the invention.

The following Table 4 shows the comparative stability of the solution of antithrombin III from freeze-dried phials reconstituted with water, within the same production lot with and without inactivation:

TABLE 4

Comparative stability at 25° C. of ATIII in solution

| PRODUCT | DAYS AT 25° C. | | | |
|---|---|---|---|---|
| | 0 | 5 | 15 | 30 |
| Inactivated ATIII | | | | |
| Activity (IU/ml) | 17.3 | 17.4 | 14.4 | 11.4 |
| Initial % | 100 | 101 | 83 | 66 |
| NON-ACTIVATED ATIII | | | | |
| Activity (IU/ml) | 18 | 20.9 | 11.4 | 8.2 |
| Initial % | 100 | 116 | 63 | 46 |

As a final general summing-up, all the assays showed absence of structural or functional alteration of the protein molecule.

Example 4

The protective action of sodium chloride and other compounds was shown by inactivation treatment at different concentrations of the said stabiliser in the presence of antithrombin III, by determining the recovery of biological activity (the chromogenic substrate method).

5.00 g fractions were taken of a solution of purified antithrombin III from a single production lot (no. 305690) and increasing quantities of the following stabilisers—sodium chloride, sodium citrate and mannitol—were added as per Table 5. The stabilised solution was cooled in a water/ice bath to between 2 and 4° C., followed by addition of 2N sodium hydroxide until the pH was 12.50±0.05. Under these conditions the samples were incubated for 1 hour and then neutralised with 2N hydrochloric acid to pH 7.0±0.2. The recovery of antithrombin III activity was determined in the samples before and after inactivation treatment.

The results of recovery are shown in the following Table 5.

TABLE 5

Recovery of ATIII activity during inactivation treatment at pH 12.5 for 1 hour

| STABILISER | ADDITION OF STABILISER TO THE ATIII SOLUTION (g/l) | % RECOVERY ATIII |
|---|---|---|
| Sodium chloride | 5.85 | 15.5 |
| Sodium chloride | 29.3 | 21.6 |
| Sodium chloride | 87.8 | 36.7 |
| Sodium chloride | 175.5 | 94.4 |
| Sodium citrate | 20 | 33.8 |
| Sodium citrate | 50 | 35.4 |
| Sodium citrate | 100 | 42.6 |
| Sodium citrate | 190 | 52.0 |
| Mannitol | 20 | 22.6 |
| Mannitol | 50 | 27.6 |
| Mannitol | 100 | 38.1 |
| Mannitol | 200 | 40.2 |
| Sodium chloride/sodium citrate | 175.5/20.0 | 97.6 |
| Sodium chloride/sodium citrate | 175.5/50.0 | 98.0 |
| Sodium chloride/sodium citrate | 175.5/100.0 | 96.5 |
| Sodium chloride/sodium citrate | 175.5/190.0 | 96.3 |
| Sodium chloride/sodium citrate | 175.5/250.0 | 95.4 |
| Sodium chloride/sodium citrate | 175.5/300.0 | 97.4 |

The results show the protective effect of sodium chloride or mixtures thereof with smaller quantities of other salts such as sodium citrate, capable of giving sufficient stability to the protein. The optimum stabilising composition will be that which preserves the ATIII activity and has the minimum protective effect on viruses. This is achieved by using the smallest possible concentration of stabilisers that do not protect the virus (sodium chloride). The optimum composition will correspond to that obtained by addition of 175.5 g sodium chloride per liter of actual solution (or 3 mols of salt) or even better by adding it to the previous 20.0 g of trisodium citrate dihydrate (0.067 mols per liter of actual solution).

Example 5

This example shows the possibility of using the same method to inactivate other proteins in the group comprising inhibitors of serine-protease enzymes such as α1 antitrypsin (or α1 PI).

To this end, the protective effect of sodium chloride was tested with regard to the protease inhibitor (α1 PI), by monitoring the recovery of its anti-elastase activity at various concentrations of the stabiliser.

The starting purified solution of α1 PI (specific activity 1.05 IU/ml: $A_{280\ nm}$) had an anti-elastase activity of 8.8 IU/ml. 20.0 ml fractions of this solution were taken and stabilised by adding increasing quantities of sodium chloride to the solution. After dissolution, the substance was cooled in a water/ice bath to a temperature between 2 and 4° C., and the viruses were inactivated by adding 2N sodium hydroxide until the pH was 12.50±0.05. After incubation for 1 hour under these conditions, the samples were neutralised by direct addition of 2N hydrochloric acid. Samples of the inactivated fractions were taken and their anti-elastase activity, specific activity and recovery were determined.

The results are given in the following Table 6:

TABLE 6

Viral inactivation of α1 PI: 1 hour at pH 12.5 at 2–4° C.

| Addition of sodium chloride | | Anti-elastase activity | Specific activity | % recovery α1 PI (anti- |
|---|---|---|---|---|
| (g per liter) | (mols per liter) | (IU/ml) | (IU/ml:$A_{280}$) | elastase) |
| 0 | 0 | 2.12 | 0.25 | 24 |
| 29.3 | 0.5 | 2.50 | 0.29 | 28 |
| 58.5 | 1 | 2.66 | 0.34 | 32 |
| 117 | 2 | 9.13 | 1.17 | 112 |
| 234 | 4 | 8.21 | 1.10 | 105 |

Sodium chloride has a marked protective effect (values>100% recovery and specific activity>1.5 IU/ml:$A_{280}$) at concentrations of 2 and 4 mols per liter.

Example 6

Other proteins with a molecular structure similar to inhibitors of serine-protease enzymes were investigated. Albumin is a non-limitative example of this group of proteins.

The process consisted in alkaline inactivation treatment of purified stabilised human albumin for intravenous injection. Two solutions, of respectively 2 and 5% proteins were prepared from the same 5% adjusted albumin solution (caprylate and tryptophanate) by dilution with physiological salt solution (0.9%). The 2% solution was divided into two fractions, and 3 mols/liter of sodium chloride was added to one of them. All the solutions were then cooled in a water/ice bath to a temperature of 2–4° C. By addition of 2N sodium hydroxide, the solutions were brought to pH 12.50±0.05, incubated for 1 hour under these conditions, and then neutralised with 2N hydrochloric acid to pH 7.0±0.2.

Next, the sample having the highest concentration of salt was dialysed in a Cuprofan cartridge (make 1 DEL M-II) against a solution of stabilisers (caprylate and tryptophanate) at equal concentration containing the albumin solution, the ionic strength being sufficiently reduced to the physiological value. After adjustment of the ionic strength, the solutions were concentrated by ultrafiltration (TFF PrepScale by Millipore) with a 10 kD membrane to 5% of protein. Readjustments were made in the concentrations of stabilisers, protein (5%), isotonicity (0.15 M sodium chloride) and pH 7.0±0.2, of the samples in each assay. The final step was filtration through a 0.22 μm sterile membrane (PVDF by Millipore) into 50 ml phials, which were then pasteurised for 10 hours at 60±0.5° C.

Samples of the solution and the control (without inactivation treatment) were taken at each protein and salt concentration of the assays. The molecular composition (molecular distribution HPLC) and the stability of the final product were evaluated.

The results are given in Table 7.

TABLE 7

Viral inactivation of albumin: 1 hour at pH 12.5 and 2–4° C.

| Concentration of albumin (%) | Concentration of sodium chloride | | Turbidity (NTU) | Aggregation (HPLC) (% polymers) | | Assay (1) Stability (Δ NTU) |
|---|---|---|---|---|---|---|
| | (g per liter) | (mols per liter) | | Direct | Corrected | |
| 5 | 8.8 | 0.15 | 35 | 12.40 | 4.71 | 10 |
| 2 | 8.8 | 0.15 | 32 | 9.66 | 3.86 | 10 |
| | 184 | 3.15 | 17.9 | 0 | 0 | 0.4 |
| Control | | (not inactivated) | 9.4 | 14.56 | 5.38 | 0 |

(1) Test of stability: determination of increase in turbidity after the albumin solution was treated at 56° C. for 50 hours.

Example 7

The range of pH values at which viral inactivation was possible, and the exposure time, were determined.

A starting solution of purified antithrombin III (specific activity>6 IU/mg protein) was inactivated at various pH, temperatures and exposure times, by adding 2N sodium hydroxide to the solutions after they had been stabilised with sodium chloride and citrate. The solutions were then neutralised and samples were taken in order to monitor their ATIII activity. The recovery of activity after each treatment was calculated.

The precise conditions of the process and the results are given in Table 8 hereinafter:

TABLE 8

% Recovery of ATIII activity at various pH, incubation times and temperatures

| STABILISERS | ADDITION OF STABILISERS (g/l) | TEMPERATURE (° C.) | INCUBATION TIME (hours) | pH | % RECOVERY OF ATIII ACTIVITY |
|---|---|---|---|---|---|
| Sodium chloride + Sodium citrate | 58.5 + 190.0 | 4 | 20 | 10.0 | 99.7 |
| | | | | 11.0 | 91.7 |
| | | | | 12.0 | 85.2 |
| | | 25 | 20 | 10.0 | 100.2 |
| | | | | 11.0 | 90.3 |
| | | | | 12.0 | 27.6 |
| | 34.5 + 190.0 | 4 | 20 | | 54.8 |
| | | | 12 | 12.0 | 92.8 |
| | | | 4 | | 99.7 |
| | | | 1 | | 96.3 |
| | | | 4 | | 83.7 |
| | | | 1 | 12.5 | 92.0 |
| | | | 1 | 13.0 | 60.2 |
| Sodium chloride + Sodium citrate + Mannitol | 5.0 + 5.2 + 20.0 (isotonic formula) | 4 | 20 | 12.0 | 8.3 |
| | 175.5 + 20.0 + 20.0 | 4 | 1 | 13.0 | 88.5 |
| | 204.8 + 20 + 20 | 4 | 1 | 13.0 | 91.6 |
| | 234.0 + 20.0 + 20.0 | 4 | 1 | 13.0 | 90.3 |
| | 175.5 + 17.0 + 20.0 | 4 | 1 | 12.5 | 97.3 |
| | 204.8 + 17.0 + 20.0 | 4 | 1 | 12.5 | 97.4 |
| | | | | 12.66 | 91.8 |

I claim:

1. A method for reducing the number of active viral contaminants in a solution comprising one or more biologically active blood proteins, said proteins being from human or animal origin or obtained by recombinant DNA technology, said method comprising:
adding to a solution comprising a biologically active protein one or more inorganic salts in an amount sufficient to stabilize said protein in a solution with a pH of between pH 10 and pH 14, and an amount of an alkaline solution sufficient to raise the pH of said protein solution to between pH 10 and pH 14; and
incubating said protein solution for an amount of time sufficient to inactivate said virus contaminants wherein said protein maintains its biological activity.

2. The method of claim 1, wherein said protein is purified protein, and wherein said protein does not contain denaturing substances.

3. The method of claim 1, further comprising adding an acidic solution in an amount sufficient to reduce the pH of said protein solution to below pH 10, after said incubating.

4. The method of claim 3, further comprising removing said inorganic salts from said protein solution.

5. The method of claim 4, wherein said inorganic salts are removed from said protein solution by dialysis or diafiltration.

6. The method of claim 3 wherein said incubating takes between 1 second and 100 hours.

7. The method of claim 6, wherein said incubating takes between 1 minute and 60 minutes.

8. The method of claim 3, wherein the pH of said protein solution is reduced to about pH 7.

9. The method of claim 3, wherein said acidic solution comprises a member selected from the group consisting of mineral and organic acids.

10. The method of claim 9 wherein said acidic solution is comprised of hydrochloric acid.

11. The method of claim 1, wherein said protein is present in said protein solution at a concentration between 0.001% and 25% weight to volume.

12. The method of claim 11, wherein said protein is present in said protein solution at a concentration between 0.1% and 5% weight to volume.

13. The method of claim 1, wherein said inorganic salts are members selected from the group consisting of neutral ionic salts, non-neutral ionic salts, and mixtures thereof.

14. The method of claim 13, wherein said neutral ionic salt is sodium chloride.

15. The method of claim 13 wherein said salt is a neutral ionic salt, and wherein after the addition of said neutral ionic salt to said protein solution said neutral ionic salt is present in said protein solution at a concentration between 0.005 M and the concentration at which said neutral ionic salt forms a saturating solution in water.

16. The method of claim 15 wherein said neutral ionic salt is sodium chloride and wherein after the addition of said sodium chloride to said protein solution said sodium chloride is present in said protein solution at a concentration between 1 and 4 M.

17. The method of claim 1 wherein said protein solution is maintained at a temperature between 0° C. and 45° C.

18. The method of claim 17 wherein said protein solution is maintained at a temperature between about 2° C. and 4° C.

19. The method of claim 1 wherein said alkaline solution comprises an alkali metal hydroxide.

20. The method of claim 19 wherein said alkali metal hydroxide is present in said alkaline solution at a concentration between about 0.001 M and the concentration at which said alkali metal hydroxide forms a saturating solution in water.

21. The method of claim 1 wherein said pH of said protein solution is raised to between pH 12 and pH 13 by said alkaline solution.

22. The method of claim 1, wherein after said incubating step said protein possesses at least 90 percent of said protein's original biological activity.

23. The method of claim 1, wherein said amount of said inorganic salt is between about 2 and about 4 moles per liter of said solution.

24. The method of claim 1, wherein said inorganic salts are selected from the group consisting of chloride salts of alkali metals, sulfate salts of alkali metals, ammonium chloride, and ammonium sulfate.

25. The method of claim 1, wherein said amount of said inorganic salt is between about 2 and about 4 moles per liter of said solution, said inorganic salts are selected from the group consisting of chloride salts of alkali metals, sulfate salts of alkali metals, ammonium chloride, and ammonium sulfate, and wherein after said incubating step said protein possesses at least 90 percent of said protein's original biological activity.

26. A method for reducing the number of active viral contaminants in a solution comprising one or more biologically active blood proteins, said proteins being from human or animal origin or obtained by recombinant DNA technology, said method comprising:

stabilizing a solution of said biologically active protein in water by the addition of a neutral ionic salt to said protein solution, wherein the concentration of said protein in said protein solution is between 0.1% and 5% weight to volume, and wherein the concentration of said neutral ionic salt is between 1 M and 4 M;

adding an amount of an alkali-metal hydroxide solution sufficient to raise the pH of said protein solution to between pH 10 and pH 14; and incubating said protein solution for a period of time between 1 minute and 60 minutes, said period of time being sufficient to inactivate said virus contaminants.

27. The method of claim 26 which further comprises adding an amount of a solution comprised of a member selected from the group consisting of mineral and organic acids to said protein solution, said amount of solution being sufficient to reduce the pH of said protein solution to between pH 7 and pH 10.

* * * * *